(12) United States Patent
Verbeek

(10) Patent No.: US 11,559,664 B2
(45) Date of Patent: *Jan. 24, 2023

(54) INSTRUMENT FOR ENDOSCOPIC APPLICATIONS

(71) Applicant: Fortimedix Assets II B.V., Geleen (NL)

(72) Inventor: Marcel Antonius Elisabeth Verbeek, Heerlen (NL)

(73) Assignee: Fortimedix Assets II B.V., Geleen (NL)

( * ) Notice: Subject to any disclaimer, the term of this patent is extended or adjusted under 35 U.S.C. 154(b) by 188 days.

This patent is subject to a terminal disclaimer.

(21) Appl. No.: 16/591,773

(22) Filed: Oct. 3, 2019

(65) Prior Publication Data

US 2020/0030576 A1 Jan. 30, 2020

Related U.S. Application Data

(62) Division of application No. 16/401,127, filed on May 2, 2019, which is a division of application No. (Continued)

(51) Int. Cl.
| | |
|---|---|
| *A61M 25/01* | (2006.01) |
| *A61B 1/00* | (2006.01) |
| *A61M 25/00* | (2006.01) |
| *A61B 1/005* | (2006.01) |
| *A61B 17/00* | (2006.01) |

(52) U.S. Cl.
CPC ....... *A61M 25/0138* (2013.01); *A61B 1/0011* (2013.01); *A61B 1/0055* (2013.01); (Continued)

(58) Field of Classification Search
CPC . A61B 1/0055; A61B 1/00071; A61B 1/0011; A61B 1/00073; A61M 25/0013; (Continued)

(56) References Cited

U.S. PATENT DOCUMENTS

| | | |
|---|---|---|
| 6,086,773 A | 7/2000 | Dufresne et al. |
| 6,107,004 A | 8/2000 | Donadio, III |

(Continued)

FOREIGN PATENT DOCUMENTS

| | | |
|---|---|---|
| DE | 10 2007 019 779 A1 | 10/2007 |
| EP | 0916359 A1 | 5/1999 |

(Continued)

OTHER PUBLICATIONS

International Search Report dated Nov. 18, 2008, in International (PCT) Application No. PCT/EP2008/005319.

*Primary Examiner* — Scott Luan

(74) *Attorney, Agent, or Firm* — N.V. Nederlandsch Octrooibureau

(57) ABSTRACT

An instrument (203; 204) for endoscopic applications. The instrument is able to be guided through a curved shaped tube (201; 202) and has an intermediate cylindrical element (3) with a handling end portion with a flexible portion and actuating means located at an actuating end portion. The intermediate cylindrical element (3) has a first cylindrical part (31; 151) at the handling end portion, a second cylindrical part (35; 155) at the actuating end portion and a number of longitudinal elements (38; 60; 70; 80; 90; 100; 110; 130; 153) for transferring the movement of the actuating means to the handling end portion. The longitudinal elements are separated by longitudinal slits in the intermediate cylindrical element.

31 Claims, 6 Drawing Sheets

Related U.S. Application Data

15/838,573, filed on Dec. 12, 2017, now Pat. No. 10,328,241, which is a division of application No. 14/614,049, filed on Feb. 4, 2015, now abandoned, which is a division of application No. 12/921,475, filed as application No. PCT/EP2008/005319 on Jun. 30, 2008, now Pat. No. 8,986,317.

(52) U.S. Cl.
CPC ...... *A61B 1/00071* (2013.01); *A61B 1/00073* (2013.01); *A61B 17/00234* (2013.01); *A61M 25/0013* (2013.01); *A61M 25/0054* (2013.01); *A61B 2017/00309* (2013.01); *A61B 2017/00314* (2013.01); *A61M 25/001* (2013.01); *A61M 2025/0004* (2013.01)

(58) Field of Classification Search
CPC ............ A61M 25/0138; A61M 25/001; A61M 25/0054
See application file for complete search history.

(56) References Cited

U.S. PATENT DOCUMENTS

| | | |
|---|---|---|
| 6,485,411 B1 | 11/2002 | Konstorum et al. |
| 6,537,459 B1 | 3/2003 | Dufresne et al. |
| 7,018,330 B2 | 3/2006 | Alekseenko et al. |
| 2003/0069522 A1 | 4/2003 | Jacobsen et al. |
| 2005/0027287 A1 | 2/2005 | O'Connor |
| 2006/0281566 A1 | 12/2006 | Lee |
| 2007/0049800 A1 | 3/2007 | Boulais |
| 2007/0255105 A1 | 11/2007 | Ochi et al. |
| 2008/0234545 A1 | 9/2008 | Breedveld et al. |
| 2009/0069632 A1 | 3/2009 | McIntyre et al. |
| 2011/0004157 A1 | 1/2011 | Dewaele et al. |

FOREIGN PATENT DOCUMENTS

| | | |
|---|---|---|
| EP | 1708609 A1 | 10/2006 |
| JP | 5-20702 U | 3/1993 |
| JP | 11-239617 A | 9/1999 |
| JP | 2007-516042 A | 6/2007 |
| WO | 97/42910 A1 | 11/1997 |
| WO | 99/53830 A1 | 10/1999 |
| WO | 99/61261 A1 | 12/1999 |
| WO | 2005/065555 A1 | 7/2005 |
| WO | 2005/067785 A1 | 7/2005 |
| WO | 2009/098244 A2 | 8/2009 |
| WO | 2009/112060 A1 | 9/2009 |
| WO | 2009/127236 A1 | 10/2009 |

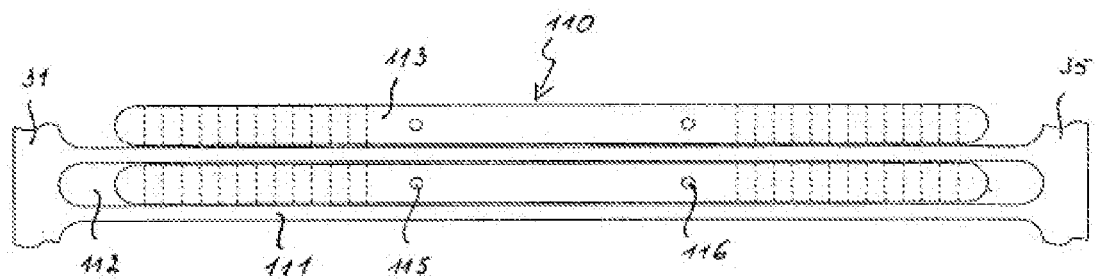
Fig. 9
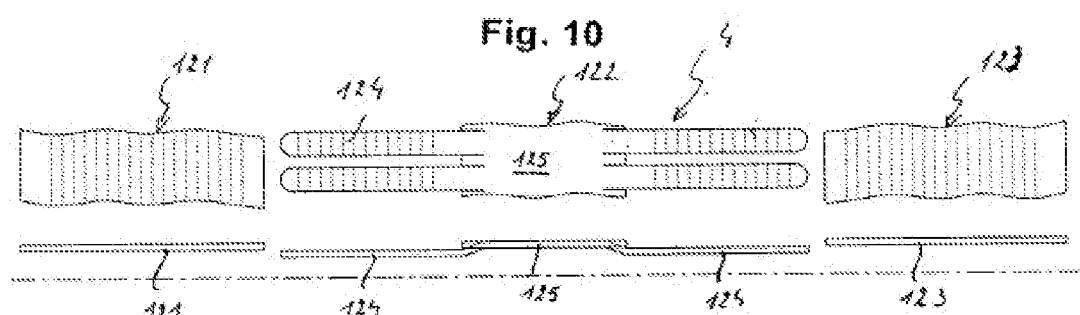
Fig. 10
Fig. 11
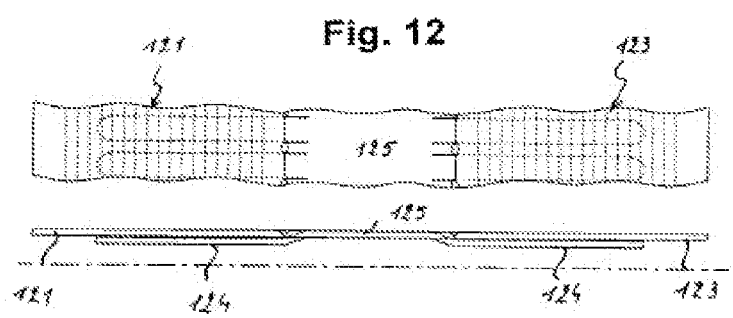
Fig. 12
Fig. 13

INSTRUMENT FOR ENDOSCOPIC APPLICATIONS

BACKGROUND

1. Field

The invention relates to an instrument for endoscopic applications.

2. Description of Related Art

Such an instrument has been described for example in EP-A-1 708 609 and is normally used for applications such as minimal invasive surgery, but it is also applicable for other purposes such as the inspection or reparation of mechanical or electronic installations at locations which are difficult to reach. In the further description the term endoscopic applications or endoscopic instrument will be used but the term must be interpreted as covering also other applications or instruments as explained above.

In the known instrument according to EP-A-1 708 609, the actuating part needed to steer one end of the instrument by movement of the other end is made out of a number of cables which are connected both to the first and second end portion. Connecting the cables to these portions is cumbersome and complicated in that each cable has to be connected separately and the tension in the cables must be the same for all cables so to obtain a reliable control of the movement. This makes the production of such an instrument complicated.

US-A1-2007/049800 discloses an articulation joint for use in a medical device such as an endoscope. In one embodiment, the articulation joint comprises a plurality of interconnected segments. Each segment comprises a cylinder with an outer wall and a central lumen. The outer wall includes a number of hinge elements therein and a series of slots there through. A plurality of cable guide elements having a passage for control cables are inserted into the slots and two or more cables are threaded through the plurality of cable guide elements and tensioned to form the articulation joint body. In another embodiment, the articulation joint is an elongated tubular body comprising a cylinder with an outer wall and a central lumen. The outer wall comprises a number of hinge elements therein and a series of slots there through. A plurality of annular rings are snap-fitted around the circumference of the tubular body at spaced intervals. Each annular ring has an outer circumference with a first end and a second end and a space there between. Also included in each annular ring is at least one pair of inwardly extending cable guide loops adapted to be inserted into the slots in the outer wall of the tubular body. Two or more cables are threaded through the plurality of cable guide loops and tensioned to form the articulation joint body. In both cases, a method of manufacturing the articulation joint involves a step of threading one or more cables through the guide elements/loops and tensioning the cables.

WO-A-97/42910 discloses a manufacturing process for an apparatus including a slotted hypotube. The manufacturing process includes creating a pattern of slots in a flexible metallic tubular member. The manufacturing process may include an additional step of encasing the flexible metallic tubular member such that a fluid tight seal is formed around the periphery of the tubular member.

WO 2009/098244 A2 that was published on 13 Aug. 2009 and claims priority of EP 08151060 that was filed on 5 Feb. 2008, discloses a steerable tube comprising a hollow elongate tubular member having a proximal end, distal end, a wall surface disposed between said proximal and distal end, a bend-resistive zone flanked by a proximal bendable zone that forms a controller and a distal bendable zone that forms an effector that moves responsive to movements of the controller, whereby the wall of the tubular member in the bend-resistive zone comprises a structure that is a plurality of longitudinal slits, forming a plurality of longitudinal strips, the wall of the tubular member in the proximal bendable zone and the distal bendable zone comprises a structure that is a plurality of longitudinal wires, at least one strip is in connection with a wire in the proximal bendable zone and a wire; in the distal bendable zone, such that translation by said wire in the controller is transmitted via the strip to said wire in the effector, a proximal annular region of the tubular member, proximal to the proximal bendable zone to which the proximal wires are anchored, a distal annular region of the tubular member distal to the distal bendable zone to which the distal wires are anchored.

SUMMARY

It is an object of the invention to provide an instrument for endoscopic applications having an improved construction compared to the instruments known in the art.

This object is achieved by an instrument defined in claim 1. The construction of the tube like member of the instrument according to the invention enables a more reliable operation of the instrument compared to instruments known in the art.

Other advantages and characteristics of the invention will be clear from the following description, reference being made to the annexed drawings.

BRIEF DESCRIPTION OF THE DRAWINGS

FIG. 9 is an unrolled view of a part of a seventh embodiment of the intermediate member according to the invention, FIG. 10 is an unrolled view of a part of an eighth embodiment of the intermediate member according to the invention in a pre-assembled condition, FIG. 11 is an cross-sectional view of the unit with an intermediate member according to FIG. 10 in the pre-assembled condition, FIG. 12 is an unrolled view of a part of the eighth embodiment of the intermediate member according to the invention in the assembled condition, FIG. 13 is an cross-sectional view of the instrument with an intermediate member according to FIG. 10 in the assembled condition.

DETAILED DESCRIPTION

Figure 1:
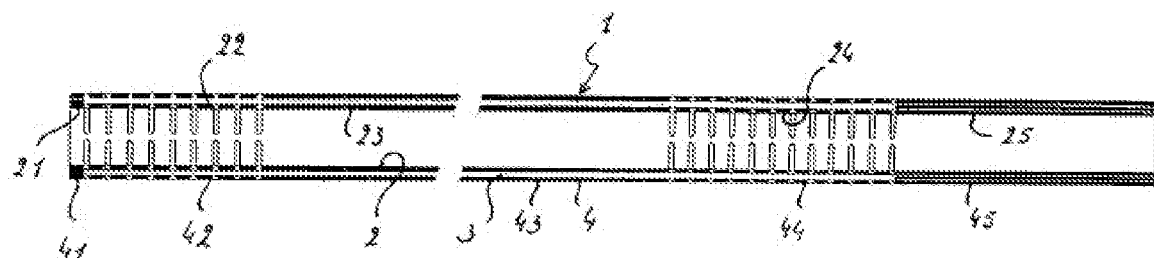
FIG. 1 is a schematic cross-section of an instrument according to the invention.

In FIG. 1 there is shown an axial cross-section of an instrument 1 according to the invention. The instrument 1 is composed of three coaxial cylindrical members an inner member 2, an intermediate member 3 and an outer member 4. The inner cylindrical member 2 is composed of a first rigid end part 21, which is the part normally used at the location which is difficult to reach or inside the human body or, a first flexible part 22, an intermediate rigid part 23, a second flexible part 24 and a second rigid end part 25 which is normally used as the operating part of the instrument in that it serves to steer the other end of the unit. The outer cylindrical member 4 is in the same way composed of a first rigid part 41, a flexible part 42, an intermediate rigid part 43, a second flexible part 44 and a second rigid part 45. The length of the different parts of the cylindrical members 2 and 4 are substantially the same so that when the cylindrical member 2 is inserted into the cylindrical member 4, the different parts are positioned against each other. The intermediate cylindrical member 3 also has a first rigid end part 31 and a second rigid end part 35 which in the assembled condition are located between the corresponding rigid parts 21, 41 and 25, 45 respectively of the two other cylindrical members.

The intermediate part 33 of the intermediate cylindrical member is formed by three or more separate longitudinal elements which can have different forms and shapes as will be explained below. After assembly of the three cylindrical members 2, 3 and 4 whereby the member 2 is inserted in the member 3 and the two combined members 2, 3 are inserted into the member 4, the end faces of the three members 2, 3 and 4 are connected to each other at both ends so as to have one integral unit.

Figure 2:
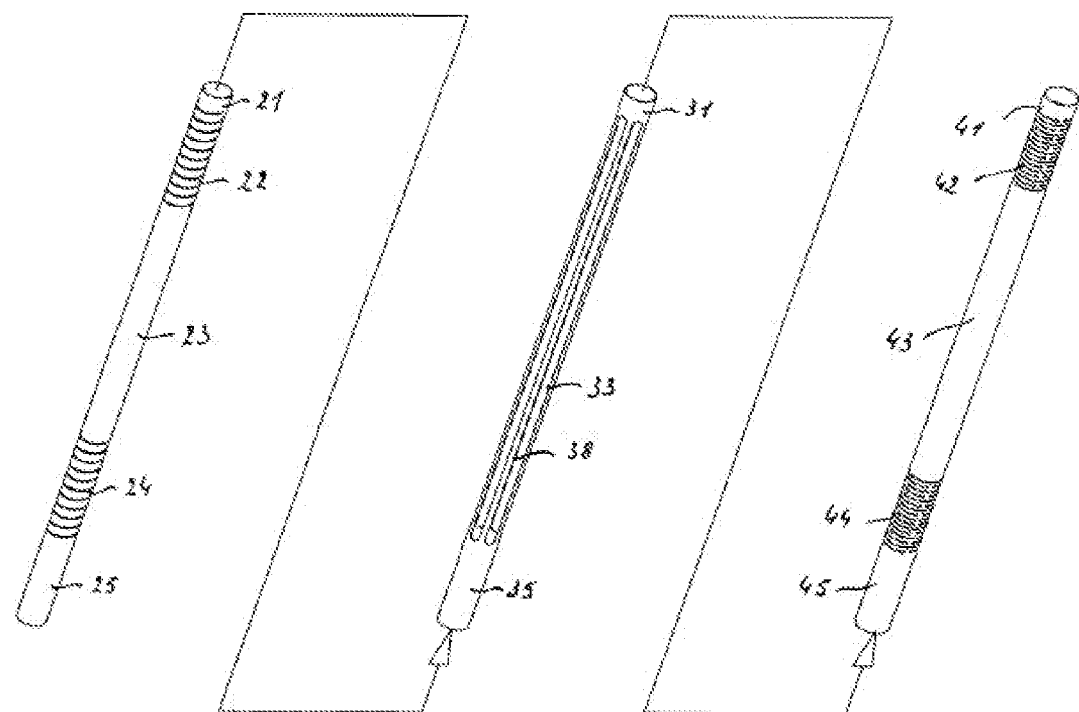
FIG. 2 is an exploded view of the three cylindrical members forming the instrument according to the invention.
Figure 3:
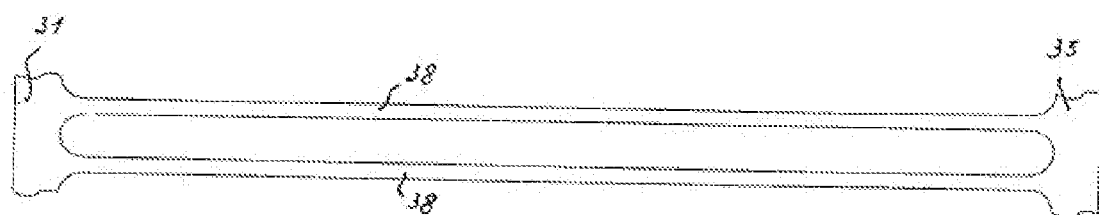
FIG. 3 is an unrolled view of a part of the intermediate cylindrical member of the instrument according to the invention.

In the embodiment shown in FIG. 2 the intermediate part 33 is formed by a number of longitudinal elements 38 with a uniform cross-section so that the intermediate part 33 has the general shape and form as shown in the unrolled condition in FIG. 3. From this it also becomes clear that the intermediate part is formed by a number of over the circumference of the cylindrical part 3 equally spaced parallel longitudinal elements 38. The number of elements 38 must be at least three, so that the instrument 1 becomes fully controllable in any direction, but any higher number is possible as well.

The production of such an intermediate part is most conveniently done by injection molding or plating techniques or starting form a regular cylindrical tube with the desired inner and outer diameter and removing these parts of the tube wall required to end up with the desired shape of the intermediate cylindrical member. This removal of material can be done by means of different techniques such as laser cutting, photochemical etching, deep pressing, conventional chipping techniques such as drilling or milling, high pressure water jet cutting systems or any suitable material removing process available. Preferably laser cutting is used as this allows a very accurate and clean removal of material under reasonable economic conditions. These are convenient ways as the member 3 can be made so to say in one process, without requiring additional steps for connecting the different parts of the intermediate cylindrical member as was required in the conventional instruments, where the longitudinal members must be connected in some way to the end parts.

Figure 19:
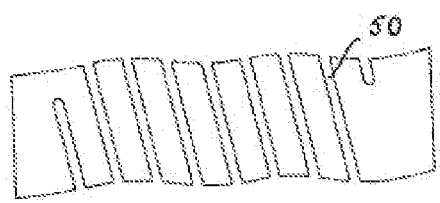
FIG. 19 is a schematic presentation of an unrolled view of a first embodiment of a flexible part of a cylindrical member as shown in FIG. 1 or 2.

The same type of technology can be used for producing the inner and outer cylindrical members 2 and 4 with their respective flexible parts 22, 24, 42 and 44. A tube having flexible parts can be obtained in different ways. In FIGS. 19, 20, 21 and 22 there are shown different how such flexibility in part can be obtained. FIG. 19 shows a schematic representation of a rolled out flexible cylindrical portion. In the embodiments shown in FIG. 19, the part of the cylindrical tube to become flexible has been provided with slits 50 extending in a helical manner over the length of the flexible part. The flexibility can be controlled by the number of slits 50 and/or the angle of the slits 50 with respect to the axial direction of the cylindrical member.

Figure 20:
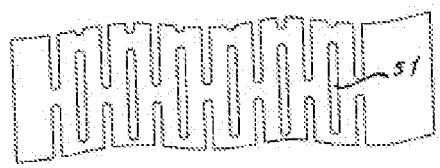
FIG. 20 is an unrolled view of a second embodiment of a flexible part of a cylindrical member as shown in FIG. 1 or 2.
Figure 21:
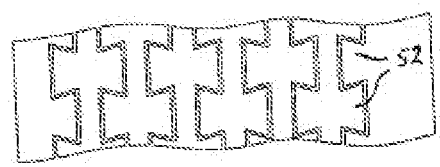
FIG. 21 is an unrolled view of a third embodiment of a flexible part of a cylindrical member as shown in FIG. 1 or 2.
Figure 22:
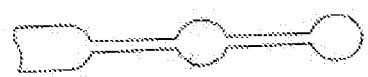
FIG. 22 is a view of a flexible part as guiding member between two longitudinal elements as shown in FIGS. 14-16.

In the embodiment of FIG. 20 the part of the cylindrical tube to become flexible has been provided with a number of short slits 51. The slits 51 can be divided into groups, the slits 51 in each group being located in the same line extending perpendicular to the axis of the cylindrical member. The slits 51 in two neighboring groups are offset. In the embodiment of FIG. 21 the part of the cylindrical tube to become flexible has been provided by making slits producing a number of swallow's tails 52 which fit into each other as shown.

It will be obvious that other systems of providing a flexible part in a cylindrical tube wall may be used as well. More specifically it is possible to use combinations of the systems shown above. Otherwise it will also be obvious that an advantageous process for producing such flexible parts in cylindrical tube may be the same process as described before with respect to the production of the intermediate part 33.

As described above in the first embodiment the longitudinal elements 38 are formed by a number of parallel elements equally spaced around the circumference of the cylindrical member. As shown in FIG. 3 a free space is available between each pair of adjacent elements 38. It is possible to use longitudinal elements 38 as shown in this figure, but in the flexible parts of the instrument there will be a tendency of the longitudinal elements 38 to move in tangential direction especially when strong curves have to be made. As a consequence of this uncontrolled movement of the longitudinal elements 38 the accuracy and the magnitude of the control of the position of the one end portion by the movement of the other end portion may be lost or is becoming more complicated. This problem can be avoided by making longitudinal elements 38 in such a way that the free space between two adjacent elements 38 is as small as possible or completely left out so that two adjacent longitudinal elements 38 are touching each other and serve as a guide for each other. A disadvantage of this system however is that a big number of longitudinal elements 38 must be present, as the cross section of these elements must be chosen in such a way that their flexibility in any direction is almost the same independent of the direction of bending. As the wall thickness of the cylindrical member is relatively small compared to the overall dimensions of the cylindrical member especially with respect to the circumference, this will result in a big number of longitudinal elements 38 as seen along the tangential direction and an increase of total bending stiffness. As the longitudinal elements 38 are touching each other in the tangential direction, this provides for a guiding of these elements upon use of the instrument.

In a modified embodiment of the longitudinal elements this problem has been avoided in a different way. In this second embodiment shown in FIG. 4 each longitudinal element 60 is composed of three portions 61, 62 and 63, co-existing with the first flexible portion 22, 42, the intermediate rigid portion 23, 43 and the second flexible portion 24, 44 respectively. In the portion 62 coinciding with the intermediate rigid portion, each pair of adjacent longitudinal elements 60 is touching each other in the tangential direction so that in fact only a narrow gap is present there between just sufficient to allow independent movement of each longitudinal element.

In the other two portions 61 and 63 each longitudinal element consists of a relatively small and flexible strip 64, 65 as seen in circumferential direction, so that there is a substantial gap between each pair of adjacent strips, and each strip 64, 65 is provided with a number of cams 66, extending in circumferential direction and almost bridging completely the gap to the next strip. Because of these cams the tendency of the longitudinal elements in the flexible portions of the instrument to shift in circumferential direction is suppressed and the direction control is complete. The exact shape of these cams 66 is not very critical, provided they do not compromise flexibility of strips 64 and 65. In view thereof any shape like a trapezium shape as shown in FIG. 4 is applicable.

Figure 4:
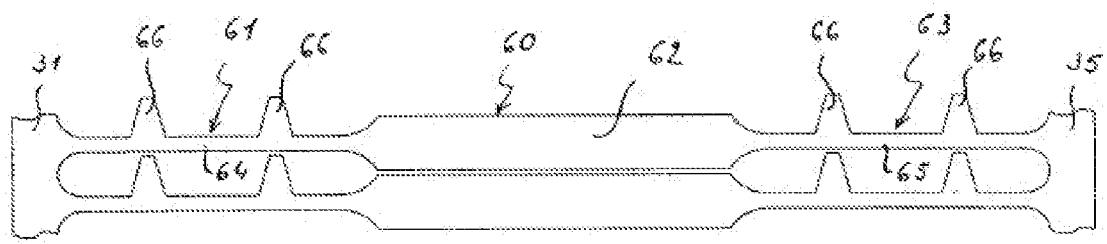
FIG. 4 is an unrolled view of a part of a second embodiment of the intermediate member according to the invention.

In the embodiment shown in FIG. 4 the cams 66 are extending towards one direction as seen from the strip to which they are connected. It is however also possible to have these cams extending to both circumferential directions starting from one strip. By using this it is either possible to have alternating types of strips as seen along the circumference, a first type provided at both sides with cams 66 extending until the next strip, and a second intermediate set of strips without cams. Otherwise it is possible to have strips with cams at both sides, where as seen along the longitudinal direction of the instrument the cams originating from one strip are alternating with cams originating from the adjacent strips. It is obvious that numerous alternatives are available. Important is that adjacent strips are in contact with each but that flexibility of strips 64 and 65 is not compromised.

Figure 5:
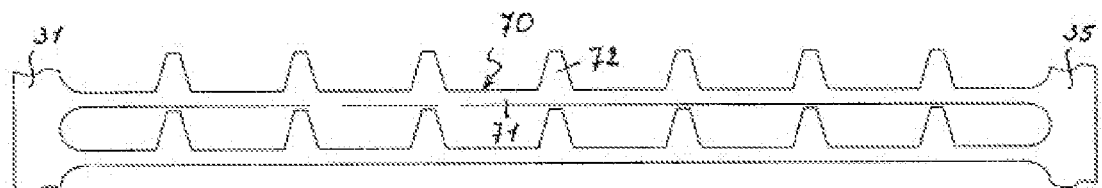
FIG. 5 is an unrolled view of a part of a third embodiment of the intermediate member according to the invention.

In FIG. 5 there is shown a third embodiment of the longitudinal elements as may be used according to the invention. In this embodiment the longitudinal elements 70 are formed by strips 71 comparable to the strips 38 of FIG. 3 interconnecting the portions 31 and 33. Furthermore the strips 71 have been provided with cams 72 so that the strips 71 are almost comparable to the strips 61 or 63 of FIG. 4. In this way a guiding is provided by the cams 72 over the complete length of the strips 71. It is obvious that also in this case the modifications with respect to the position of the cams 72 and the alternating of strips 71 with cams on both sides and strips without cams as described above with respect to FIG. 4 are also applicable for this embodiment.

Figure 6:
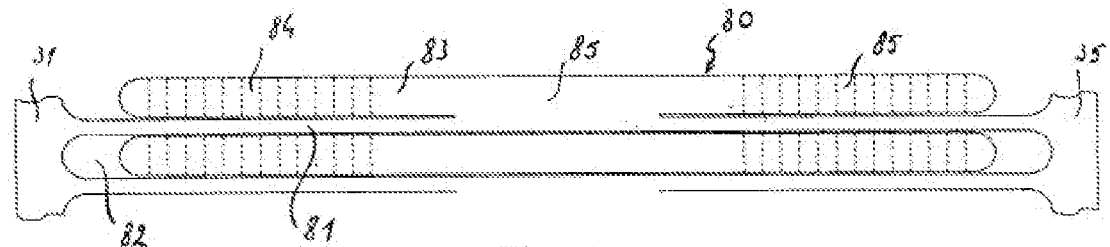
FIG. 6 is an unrolled view of a part of a fourth embodiment of the intermediate member according to the invention.

In the fourth embodiment shown in FIG. 6 the longitudinal elements 80 are formed by strips 81 interconnection the portion 31 and 35. These strips are comparable to the strips 38 in FIG. 3 and have substantially the same width. This means that between each pair of adjacent strips 81 there is left a circumferential gap 82. Each gap 82 is filled substantially by means of another strip 83, having a circumferential width slightly smaller than the circumferential width of the gap 82 and a longitudinal dimension which leaves some play between the ends of the axial ends of the strip 83 and the portions 31 and 35 respectively. The strip 85 is composed of three parts, a first flexible part 84, schematically represented with dotted lines an intermediate part 85 and a second flexible part 86, the three parts coinciding with the flexible parts 22,42, the intermediate parts 23, 43 and the flexible parts 24, 44 respectively of the instrument. The flexibility of the parts 84 and 85 may be obtained by any system described above, or a shown in FIGS. 24 and 25. The intermediate part 85 is connected to the strip 81. In this way the strip 85 is guiding the movement of the strips 81 in the flexible portions of the instrument, without hindering their longitudinal movement.

In the embodiment shown each strip 81 is on one side connected to a strip 83. As an alternative it is also possible to have a system in which as seen along the circumference of the intermediate cylindrical member this member is composed of a first set of strips 81 having both sides connected to a strip 83, and a second set of strips 81 which have no connection to such strips 83 and are as such comparable to the strips 38 of FIG. 3. It is of course obvious that other solutions are available by using combinations of strips 81 having either no, one or two connections to strips 83 by putting them in the rights sequence along the circumference of the intermediate cylindrical member.

Figure 7:
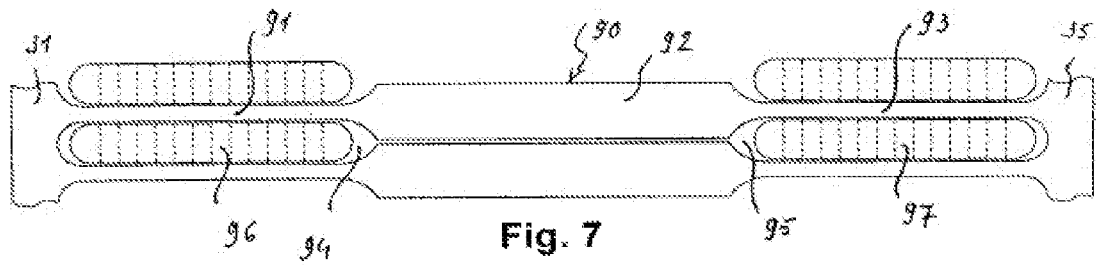
FIG. 7 is an unrolled view of a part of a fifth embodiment of the intermediate member according to the invention.

A fifth embodiment has been shown in FIG. 7. In this embodiment each longitudinal element 90 is composed of a first strip 91, a band 92 and a second strip 93. The first and second strip 91 and 93 have a circumferential width such that there is a circumferential gap 94 and 95 respectively between each pair of adjacent strips 91 and 93 respectively. The bands 92 have a circumferential width such that two adjacent bands are in contact with each other. The strips 91 and 93 coincide with the flexible portions 22, 42 and 24 and 44 respectively whereas the bands 92 coincide with the intermediate portion 23, 43. In each gap 94 and 95 respectively plates 96 and 97 respectively have been placed which plates 94, 95 have a circumferential width filling the width of the gap and thus providing a guiding for the strips 91 and 93 respectively. Free movement of the strips is achieved in that in the longitudinal direction there is some play between the axial ends of the plates 96, 97 and the portions 31, the bands 92 and the bands 92 and the portion 35 respectively.

The plates 96, 97 are completely free to move in their respective gaps 94, 95 respectively, but because of the selected dimensions only a movement in longitudinal direction is available. For the production of such a system as shown in FIG. 7 it is possible to first make the intermediate cylindrical elements by means of one of the production techniques described above, which results in an intermediate cylindrical member which is different from the one shown in FIG. 7 in that one point of each plate 96 and 97 is still connected either to an adjacent strip, to a band or to the portions 31 or 35. In this form the instrument is assembled whereby the connection point between the plates 96 or 97 and the remaining of the intermediate cylindrical member is coinciding with a hole provided in the cylindrical member 4. Once the assembling being finished the connection mentioned above can be destroyed for example by using one of the production techniques mentioned above. In this way the plates 96, 97 become completely free movable in their gaps. Here once more it will be obvious that the laser technology is very effective in this production step.

Figure 8:
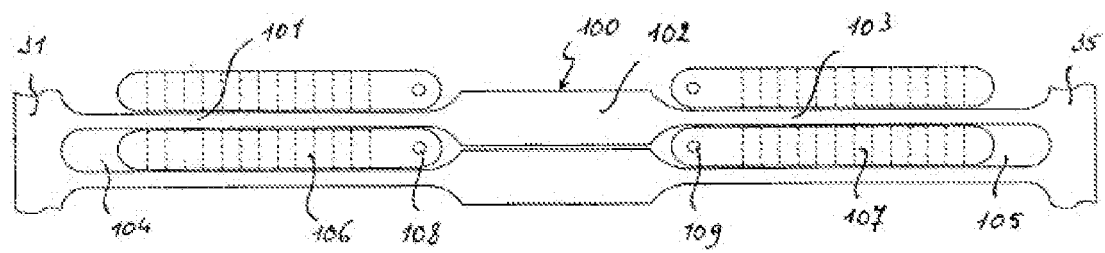
FIG. 8 is an unrolled view of a part of a sixth embodiment of the intermediate member according to the invention.

In FIG. 8 there is shown a sixth embodiment of the intermediate cylindrical member according to the invention. This embodiment is very similar to the embodiment shown in FIG. 7, in that the longitudinal elements 100 are composed of strips 101 and 103 comparable to the strips 91 and 93, and a band 102 comparable to the band 92. In the same way, the gaps 104 and 105 are comparable to the gaps 94 and 95 occupied by plates 106 and 107 and comparable to the plates 96 and 97. In this embodiment the plates 106 and 107 are not completely free from the remaining of the instrument, but each plate 106 and 107 is connected either to the outer cylindrical member 4 or to the inner cylindrical member 2, especially in the non-flexible part thereof. In the embodiment shown this has been achieved by welding at one point 108 and 109 respectively the plates 106 and 107 to the intermediate rigid portion of either the inner or outer cylindrical member 2 or 4. In this way the strips 101 and 103 are accurately guided by the plates 106 and 107 in the flexible portions of the instrument by the plates 106 and 107, but the plates 106 and 107 are not free to move whereby the control of movement has been improved and the assembling of the instrument becomes much easier.

The embodiment shown in FIG. 9, the seventh embodiment can be seen as a combination of the embodiment of FIG. 6 and the embodiment of FIG. 8. The longitudinal element 110 consists of a number of strips 111, comparable to the strips 81 and the gap 112 between each pair of adjacent strips 111 is occupied by a strip or plate 113 comparable to strip 83. In this embodiment the strips 113 are not connected to the strips 111 as in the embodiment of FIG. 6, but are connected at some points 115, 116 to rigid intermediate part of either the outer or inner cylindrical member 2 or 4 of the instrument comparable to the embodiment of FIG. 8.

In FIGS. 10, 11, 12 and 13 there is shown an embodiment of the instrument which can be seen as a modification of the embodiment shown in FIG. 9. In the FIGS. 10 and 11 there is shown situation before assembly whereas the FIGS. 12 and 13 show the assembled instrument.

In FIGS. 10 and 11 there is shown the outer cylindrical element 4, which is composed of three parts, a part 121 forming the first flexible portion 42 and the first rigid portion 41, a part 122 forming the intermediate rigid portion 43 and also forming the guiding plates 124 comparable to the guiding plates 106, 107 in FIG. 8 and a part 123 forming the second flexible part 44 and the second rigid part 45.

The parts 121 and 123 are simple cylindrical tubes which have been provided with a flexible portion by one of the methods described above. The intermediate portion 122 is formed by a cylindrical tube in which by one of the processes described above for removal of material a number of tongues 124 have been made which have been made flexible by one of the methods described above. These tongs extend from both ends of a central portion and will form bands which will occupy the space between strips like the strips 11. Therefore the tongues have been deformed at their connection with the central portion 125 so as to have a smaller diameter whereby these tongues fit into the spaces between the strips. In fact the tongues are deformed to form an internal and external diameter substantially equal to the corresponding diameters of the strips.

After the different part 121, 122 and 122 have been produced as described, the parts 121 and 122 are moved over the tongues 124 and the abutting ends of the part 121 and 125 and the part 125 and 123 are welded together so as to form the external cylindrical member 4.

Figure 14:
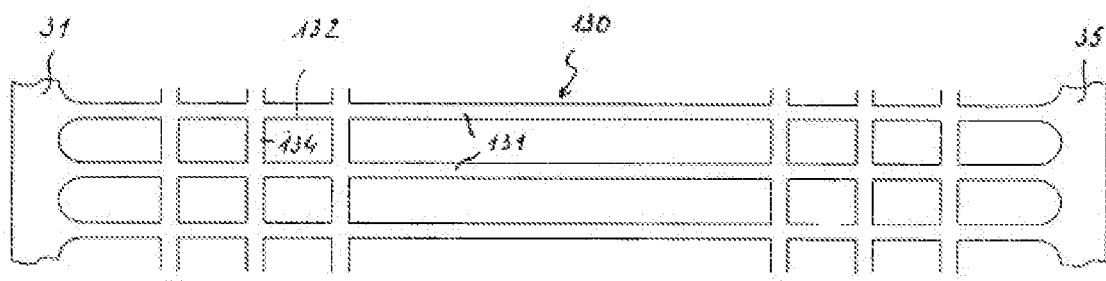
FIG. 14 is an unrolled view of a part of a ninth embodiment of the intermediate member according to the invention in a pre-assembled condition.
Figure 15:
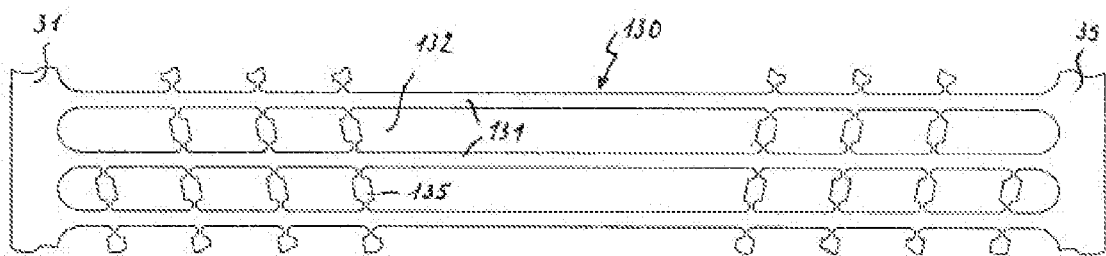
FIG. 15 is an unrolled view of a part of a tenth embodiment of the intermediate member according to the invention.
Figure 16:
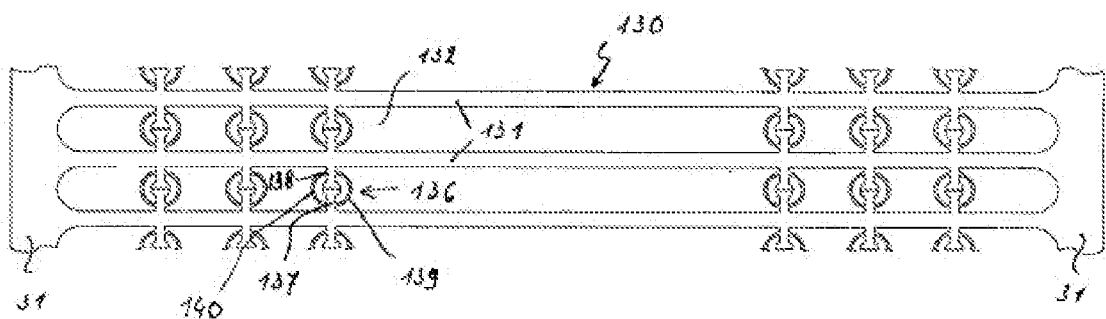
FIG. 16 is an unrolled view of a part of an eleventh embodiment of the intermediate member according to the invention.

In FIGS. 14, 15 and 16 there is shown a different category of embodiments of longitudinal elements 130 interconnecting the portions 31 and 35 of the intermediate cylindrical member 3. The longitudinal elements 130 are formed by strips 131 comparable to the strips 38 of FIG. 3. As seen in the circumferential direction of the cylindrical member, these strips are space apart from each other by a gap 132. At least in the flexible zone of the instrument where a guiding of the strips is preferred or required, each pair of adjacent strips is connected by a number of bridges which have a defined degree of flexibility as seen in the longitudinal direction. These bridges are bridging the width of the gap 132 and can be shaped in different ways.

Figure 23:
FIG. 23 is a view of an embodiment a flexible part as guiding member as modified with respect to FIG. 22.

In the embodiment of FIG. 14 the bridges have the form of short strips 134 extending in circumferential direction and having a width in longitudinal direction which allows some parallel movement from one strip 131 to its adjacent strip 131. By selection the number of strips 134 and its cross-section dimensions its flexibility may be sufficient to allow sufficient freedom of movement of the adjacent strips 131. If needed the flexibility of the strips 134 can be enhanced by applying some special configurations as shown in FIGS. 23, 24 and 25. The strips need not to transfer any tangential force from the one strip to its adjacent strip 131, but serves only to maintain the distance between two adjacent strips 131.

In the embodiment shown in FIG. 15 the strips 135 have been shaped with some recesses so as to increase their flexibility. Moreover these strips have been not directed along the circumferential direction of the cylindrical member, bur are positioned under a small angle with respect to that direction in a way that the series of connectors form a spiral. A special shape of the bridges has been shown in the embodiment of FIG. 16. The bridges 136 of this embodiment consists of two cams 137 and 138 extending from two adjacent strips 131 and abutting about halfway in the gap between the two strips. Two semicircular bands 139 and 140 are connecting the cam 138 with the cam 137. This provides a high degree of flexibility whereas the distance between the two adjacent strips is accurately maintained. The making of such bridges 136 does not offer any special problem when using one of the techniques described above.

Figure 17:
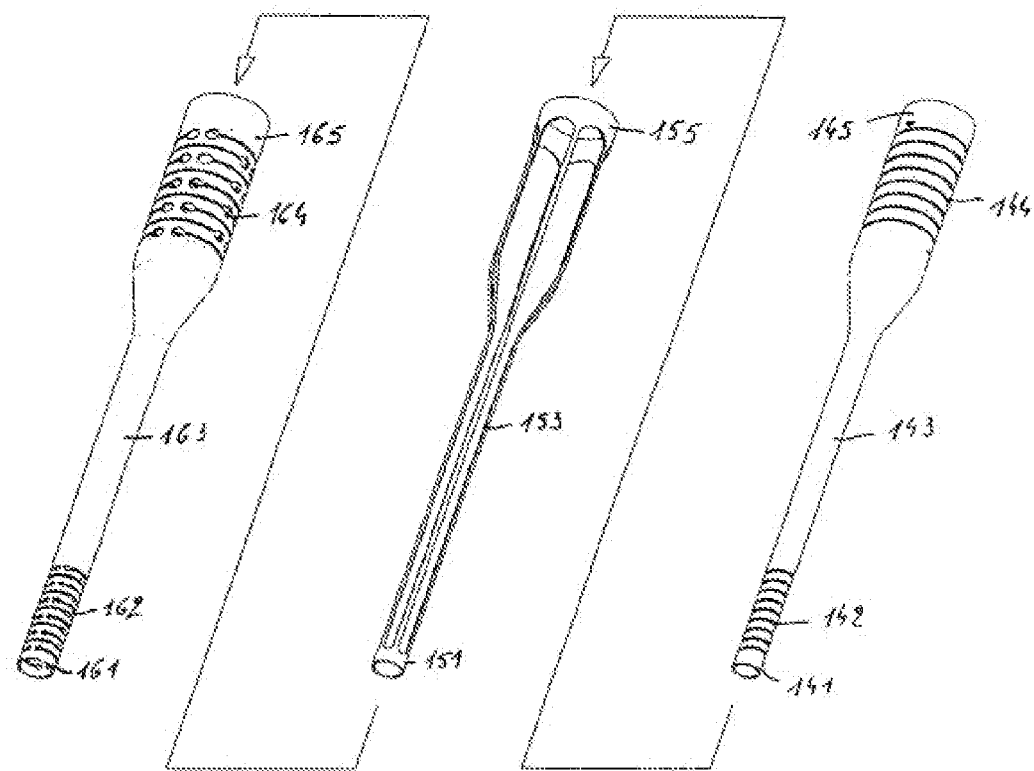
FIG. 17 is a schematic exploded view of a modified embodiment of the instrument according to the invention.

In FIG. 17 there is shown a special embodiment of an instrument according to the inventions. The inner cylindrical member is composed of a first rigid end part 141, a first flexible part 142, an intermediate rigid part 143, a second flexible part 144 and a second rigid end part 145 which is normally used as the operating part of the instrument in that it serves to steer the other end of the unit. The outer cylindrical member is in the same way composed of a first rigid part 161, a flexible part 162, an intermediate rigid part 163, a second flexible part 164 and a second rigid part 165. The intermediate cylindrical member also has a first rigid end part 151 and a second rigid end part 155 which in the assembled condition are located between the corresponding rigid parts 141, 161 and 145, 165 respectively of the two other cylindrical members. In the embodiment shown the longitudinal elements 153 are of the type shown in FIG. 3, but it will be obvious that any other type described above may be used as well. So far the construction is comparable to the instrument shown in FIG. 1.

The main difference with respect to the embodiment of FIG. 1 consists in the use of a different set of diameters for some parts of the instrument. IN the embodiment shown the parts 144, 145, 155, 164 and 165 have a larger diameter than the other parts and in the parts 143, 153 and 163 as frusto-conical portion have been made in order to connect the small diameter parts with the large diameter parts. As shown in FIG. 17 the different parts can easily be assembled by inserting one into the other. The main reason however to have such an instrument with different diameters is that by using an operating part with a larger diameter, the movement of the other end is amplified, whereas if a smaller diameter is used the movement of the other end is reduced. Dependent of the application and its requirements larger diameters can be used to have the amplified movement or smaller diameters can be used to reduce the movement and increase accuracy.

Figure 18:
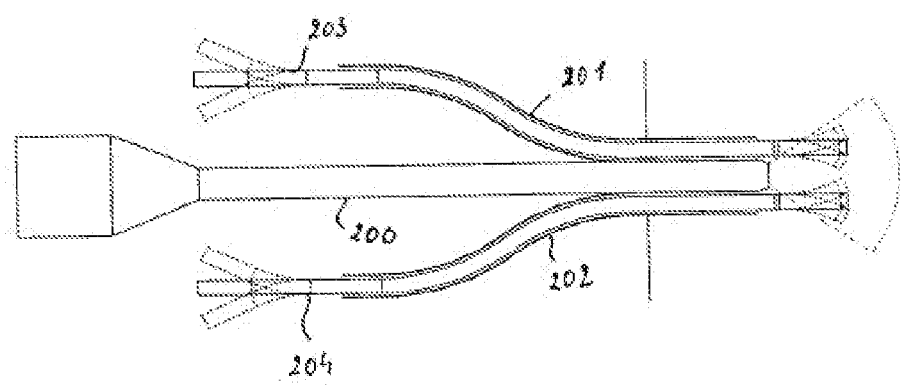
FIG. 18 is a schematic drawing of a special application of a modified instrument according to the invention.

A special application of the instrument according to the invention is shown in FIG. 18. In this application a number of tubes have been inserted into a body of an environment where some inspection or treatment must take place. In the embodiment shown there are three tubes, a first or central tube 200, which may be a straight tube which is used for illumination and viewing purposes. Two S-shaped tubes 201 and 202 are positioned partly against this central tube 200, and these tubes are used for the guiding of instruments according to the invention. The bending is necessary to have the handling side of the instruments 203 and 204 removed from each other and from the central tube 200 so that the movement is possible in any direction. By positioning the S-shaped tubes diametrically in opposition to the central tube 200 there is also sufficient space left at the working side to perform all kind of movement of these ends of the instruments 203 and 204.

In order to enable the instruments to be guided through such a S-shaped tube 201 or 202 or tubes with any curved shape, the intermediate rigid portion of the instruments 203 and 204 has been provided with at least one additional flexible portion dividing the intermediate portion in rigid portions of a lesser length so at to allow some additional bending. If needed more than one intermediate flexible portion may be included.

In EP 2,273,911 A, the first application from which the present invention is divided, different aspects were described. They were as follows.

According to a first aspect, there is provided a process for producing the actuating part of an instrument for endoscopic applications or the like, which instrument comprises a tube like member having a handling end portion with a flexible portion and actuating means located at the other end portion, which actuating means comprises a cylindrical part connected to the handling end portion, a cylindrical part connected to the actuating means and a number of longitudinal elements for transferring the movement of the actuating means to the handling end portion, characterized in that the actuating means is made starting from of a full cylindrical tube which is provided with a number of longitudinal slits thereby forming the longitudinal elements.

In an embodiment, the longitudinal slits are made by means of any known material removal techniques such as photochemical etching, deep pressing, chipping techniques preferably by laser cutting.

According to a second aspect, there is provided an instrument for endoscopic applications or the like obtained by means of the above process wherein the longitudinal slits between two neighboring longitudinal elements have such a small width that the longitudinal elements are kept parallel by each other upon actuation of the instrument.

In an embodiment, in the instrument for endoscopic applications or the like obtained by means of that process at least one longitudinal slit between a pair of neighboring longitudinal elements is provided with elements keeping the longitudinal elements parallel to each other.

In an embodiment, the at least one of a neighboring pair of longitudinal elements is provided with protrusions extending in the direction of the other longitudinal element.

In an embodiment, the protrusions are only present in the parts of the longitudinal element which are coinciding with the flexible portions of the instrument.

In an embodiment, in at least part of the non flexible part of the instrument the longitudinal elements have such a width that they substantially fill up completely the width of the longitudinal slits.

In an embodiment, each longitudinal slit is filled with a separate longitudinal element, having flexible portions coinciding at least with the flexible parts of the instrument.

In an embodiment, each separate longitudinal element has a central part coinciding with a non flexible part of the instrument which is connected to a non flexible part of the instrument, preferably to one of the adjacent longitudinal elements.

In an embodiment, in the at least part of the non flexible part of the instrument the longitudinal elements have such a width that they substantially fill up completely the width of the longitudinal slits, and in that each of the remaining parts of the longitudinal slits are filed up with separate longitudinal elements.

In an embodiment, one end of each of the separate longitudinal elements is connected to a non flexible part of the instrument.

In an embodiment, each pair of adjacent longitudinal elements is interconnected by means at least one flexible bridge, at least in the parts coinciding with the flexible parts of the instrument.

In an embodiment, the longitudinal elements in the zone adjacent the handling end portion are located in a cylindrical plane with a first diameter, in the zone adjacent to the actuating end portion are located in a cylindrical plane with a second different diameter, and in an intermediate zone are located in a conical plan interconnecting the two zones.

In an embodiment, the first diameter is smaller than the second diameter.

It is obvious that the invention is not restricted to the described embodiments as shown in the annexed drawings, but that within the scope of the claims modifications can be applied without departing from the inventive concept.

The invention claimed is:

1. A bendable instrument comprising:
an inner cylindrical element, an outer cylindrical element and an intermediate cylindrical element in between said inner and outer cylindrical elements;
the intermediate cylindrical element having a handling end portion and an actuating end portion opposite the handling end portion, the handling end portion having a first cylindrical part and a first flexible portion, and the intermediate cylindrical element having a plurality of strips connected to said first cylindrical part such that longitudinal movement of said strips relative to one another results in bending of the handling end portion at said first flexible portion, the strips being separated by longitudinal slits in said intermediate cylindrical element;

the inner cylindrical element having a first inner cylindrical element flexible portion aligned with said first flexible portion of said intermediate cylindrical element;

the outer cylindrical element having a first outer cylindrical element flexible portion aligned with said first flexible portion of said intermediate cylindrical element, wherein the instrument is configured in at least one of the following ways:

said first inner cylindrical element flexible portion comprises at least one first slit in said inner cylindrical element, and said first outer cylindrical element flexible portion comprises at least one second slit in said outer cylindrical element.

2. The instrument according to claim 1, wherein the at least one first or second slit extends in helical manner.

3. The instrument according to claim 1, wherein the at least one first or second slit comprises a plurality of groups of slits, each group located on a tangential line perpendicular to an axis of the instrument, with slits in neighbouring groups being offset to each other.

4. The instrument according to claim 1, wherein the at least one first or second slit comprises a plurality of slits shaped and spaced to produce a number of swallow's tails fitting into each other.

5. The instrument according to claim 1, wherein the strips in a first zone adjacent the handling end portion are located in a first cylindrical plane with a first diameter, and in a second zone adjacent to the actuating end portion are located in a second cylindrical plane with a second different diameter.

6. The instrument according to claim 5, wherein the first diameter is smaller than the second diameter.

7. The instrument according to claim 1, wherein the instrument has an intermediate portion between the handling end portion and the actuating end portion, said intermediate portion comprising at least one additional flexible portion.

8. The instrument according to claim 1, wherein said inner cylindrical element flexible portion and outer cylindrical element flexible portion are made by one or more of laser cutting, photochemical etching, deep pressing, chipping, and high pressure water jet cutting.

9. The instrument according to claim 1, wherein said longitudinal slits in said intermediate cylindrical element are made by one or more of laser cutting, photochemical etching, deep pressing, chipping, and high pressure water jet cutting.

10. The instrument according to claim 1, wherein said actuating end portion has a second cylindrical portion, said strips also being connected to said second cylindrical portion.

11. The instrument according to claim 10, wherein the actuating end portion has a second flexible portion, the inner cylindrical element having a second inner cylindrical element flexible portion aligned with said second flexible portion of said intermediate cylindrical element, and the outer cylindrical element having a second outer cylindrical element flexible portion aligned with said second flexible portion of said intermediate cylindrical element, wherein the instrument is configured in at least one of the following ways:

said second inner cylindrical element flexible portion comprises at least one third slit in said inner cylindrical element, and said second outer cylindrical element flexible portion comprises at least one fourth slit in said outer cylindrical element.

12. The instrument according to claim 1, wherein the intermediate cylindrical element comprises at least three strips.

13. A bendable instrument comprising:

an inner cylindrical element, an outer cylindrical element and an intermediate cylindrical element in between said inner and outer cylindrical elements;

the intermediate cylindrical element having a handling end portion and an actuating end portion opposite the handling end portion, the handling end portion having a first cylindrical part and a first flexible portion, and the intermediate cylindrical element having a number of strips connected to said first cylindrical part such that longitudinal movement of said strips relative to one another results in bending of the handling end portion at said first flexible portion, the strips being separated by longitudinal slits in said intermediate cylindrical element; and at least one of a pair of neighbouring strips is provided with spacer elements located in said slit and extending from one of the neighbouring strips at least partially in a circumferential direction toward the other one of the pair of neighbouring strips.

14. The instrument according to claim 13, wherein the spacer elements almost bridge completely said slit or contact the other one of the pair of neighbouring strips.

15. The instrument according to claim 13, wherein the spacer elements are at least one of cam shaped and trapezium shaped.

16. The instrument according to claim 13, wherein said one of said pair of neighbouring strips is provided with spacer elements extending in a first circumferential direction and with spacer elements extending in a second circumferential direction opposite to said first circumferential direction.

17. The instrument according to claim 13, wherein the spacer elements are only present in parts of the strips which are coinciding with the flexible portions of the instrument.

18. The instrument according to claim 13, wherein the inner cylindrical element has a first inner cylindrical element flexible portion aligned with said first flexible portion of said intermediate cylindrical element.

19. The instrument according to claim 13, wherein the outer cylindrical element has a first outer cylindrical element flexible portion aligned with said first flexible portion of said intermediate cylindrical element.

20. The instrument according to claim 13, wherein the inner cylindrical element has a first inner cylindrical element flexible portion aligned with said first flexible portion of said intermediate cylindrical element; and the outer cylindrical element has a first outer cylindrical element flexible portion aligned with said first flexible portion of said intermediate cylindrical element; and wherein the first inner cylindrical element flexible portion and/or the first outer cylindrical element flexible portion comprises at least one slit.

21. The instrument according to claim 20, wherein the at least one slit extends in a helical manner.

22. The instrument according to claim 20, wherein the at least one slit comprises a plurality of groups of slits, each group located on a single tangential line perpendicular to an axis of the instrument, with slits in neighbouring groups being offset to each other.

23. The instrument according to claim 20, wherein the at least one slit comprises a plurality of slits shaped and spaced to produce a number of swallow's tails fitting into each other.

24. The instrument according to claim 13, wherein the strips in a first zone adjacent the handling end portion are located in a first cylindrical plane with a first diameter, and in a second zone adjacent to the actuating end portion are located in a second cylindrical plane with a second different diameter.

25. The instrument according to claim 24, wherein the first diameter is smaller than the second diameter.

26. The instrument according to claim 13, wherein the instrument has an intermediate portion between the handling end portion and the actuating end portion, said intermediate portion comprising at least one additional flexible portion.

27. The instrument according to claim 13, wherein said inner cylindrical element flexible portion and outer cylindrical element flexible portion are made by at least one of laser cutting, photochemical etching, deep pressing, chipping, and high pressure water jet cutting.

28. The instrument according to claim 13, wherein said longitudinal slits in said intermediate cylindrical element are made by at least one of laser cutting, photochemical etching, deep pressing, chipping, and high pressure water jet cutting.

29. The instrument according to claim 13, wherein said actuating end portion has a second cylindrical portion, said strips also being connected to said second cylindrical portion.

30. The instrument according to claim 13, wherein the actuating end portion has a second flexible portion, the inner cylindrical element having a second inner cylindrical element flexible portion aligned with said second flexible portion of said intermediate cylindrical element, and the outer cylindrical element having a second outer cylindrical element flexible portion aligned with said second flexible portion of said intermediate cylindrical element,
    wherein said second inner cylindrical element flexible portion, and/or
    said second outer cylindrical element flexible portion comprises at least one slit.

31. The instrument according to claim 13, wherein the intermediate cylindrical element comprises at least three strips.

* * * * *